United States Patent [19]

Bernady et al.

[11] 4,140,715

[45] Feb. 20, 1979

[54] PROCESS FOR PREPARING N-(1,1-DIMETHYL-3-OXOBUTYL)ACRYLAMIDE FROM A 2-VINYL-1,3(4H)OXAZINE SULFATE

[75] Inventors: Karel F. Bernady; Paul D. Mogolesko, both of Belle Mead, N.J.

[73] Assignee: American Cyanamid Company, Stamford, Conn.

[21] Appl. No.: 920,099

[22] Filed: Jun. 28, 1978

[51] Int. Cl.$^2$ .................... C07C 29/00; C07C 102/00
[52] U.S. Cl. .................................. 260/561 N; 544/88
[58] Field of Search ................ 260/561 N; 544/88, 97

[56] References Cited

U.S. PATENT DOCUMENTS

| | | | |
|---|---|---|---|
| 3,531,525 | 9/1970 | Hoke et al. | 260/561 N |
| 3,542,867 | 11/1970 | Foecking | 260/561 N |
| 3,542,875 | 11/1970 | Raymond | 260/561 N |
| 3,575,890 | 4/1971 | Litt et al. | 544/88 |
| 3,649,688 | 3/1972 | Gordon et al. | 260/561 N |

FOREIGN PATENT DOCUMENTS 233130  2/1961  Australia ................................ 544/88

*Primary Examiner*—Allen B. Curtis
*Attorney, Agent, or Firm*—Charles F. Costello, Jr.

[57] ABSTRACT

A process is disclosed for preparing N-(1,1-dimethyl-3-oxobutyl)acrylamide which comprises (1) contacting a dispersion of 5,6-dihydro-6-hydroxy-4,4,6-trimethyl-2-vinyl-1,3,3(4H)-oxazine-3-ium sulfate (1:1) in a water-immiscible organic solvent with a neutralizing or alkalizing amount of gaseous ammonia at a temperature between about 10° C. and 25° C. to form a solution of diacetone acrylamide in said organic solvent and a precipitate of crystalline ammonium sulfate; (2) separating the crystals of ammonium sulfate; (3) cooling the organic mother liquors recovered from step (2) to about −10° C. to 20° C. to crystallize N-(1,1-dimethyl-3-oxobutyl)acrylamide therefrom; and (4) recovering the crystals of N-(1,1-dimethyl-3-oxabutyl) acrylamide, washing the recovered crystals with a cold water-immiscible organic solvent and drying the same.

6 Claims, No Drawings

PROCESS FOR PREPARING N-(1,1-DIMETHYL-3-OXOBUTYL)ACRYLAMIDE FROM A 2-VINYL-1,3(4H)OXAZINE SULFATE

BACKGROUND OF THE INVENTION

This invention relates to a process for the preparation of diacetone acrylamide, also known as N-(1,1-dimethyl-3-oxobutyl)acrylamide, by the ammonolysis of 5,6-dihydro-6-hydroxy-4,4,-6-trimethyl-2-vinyl-1,3(4H)-oxazine sulfate (1:1), which is represented by formula (I)

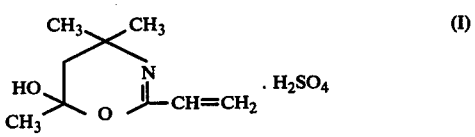

In related U.S. Patent Application, Ser. No. 920,040, filed June 28, 1978, which is incorporated by reference, the preparation of the compound of formula (I) and a new process for the preparation of diacetone acrylamide, hereafter abbreviated DIAC, utilizing the above-mentioned compound as an intermediate is disclosed. Generally, this new process comprises neutralizing or alkalizing a solution of the compound of formula (I) in a water-immiscible organic solvent with a dilute aqueous solution of an alkalizing agent, and recovering DIAC from the organic solution.

The process of this invention is different from and has advantages over the above related U.S. application process in that it is carried out under essentially nonaqueous conditions and is simpler to carry out. The essentially nonaqueous reaction condition results in less loss of the final product due to dissolution in an aqueous phase while the simplicity of the process results in increased productivity.

Applicants are not aware of any prior art reference which, in their judgment as ones skilled in the art of preparing diacetone acrylamide, would anticipate or render obvious the process of the instant invention; however, for the purpose of fully developing the background of the invention and establishing the state of the requisite art, the following references are set forth.

In U.S. Pat. No. 3,649,688, an improved method is disclosed for preparing DIAC by reacting acrylonitrile with diacetone alcohol in the presence of sulfuric acid, the improvement comprising preparing a mixture of acrylonitrile and sulfuric acid, said sulfuric acid being at least 93% concentration and the molar ratio of sulfuric acid to acrylonitrile being at least 1.6 to 1, introducing the diacetone alcohol into said mix at a temperature below 30° C. and maintaining said temperature during the reaction of the alcohol with the acrylonitrile, and recovering the DIAC from the reaction mixture. However, the product obtained is yellow-colored and contains about 5–10% by weight of by-product acrylamide.

In U.S. Pat. No. 3,542,867, an improved method is disclosed for preparing diacetone acrylamide by reacting diacetone alcohol, or mesityl oxide, or at least 2 moles of acetone in the presence of acrylonitrile and sulfuric acid, the improvement consisting of diluting the reaction mixture with water to a sulfuric acid content of 25–80% by weight, extracting the DIAC from the acidic reaction mixture with a water-immiscible organic solvent and recovering the DIAC from the extract.

In U.S. Pat. No. 3,542,875, an improved method is disclosed for preparing DIAC by reacting one mole of acrylonitrile with at least one mole of diacetone alcohol or mesityl oxide, or with at least two moles of acetone, in the presence of at least one mole of sulfuric acid, neutralizing the reaction mixture by addition of alkali to a pH at least above 7.5 and subsequently extracting with a water-immiscible organic solvent and recovering DIAC therefrom, the improvement consisting of heating the organic solution of DIAC at 50–100° C. with aqueous alkali and recovering DIAC from the organic solution.

The DIAC produced by the process of the subject invention has advantages over that produced by the processes of references U.S. Pat. Nos. 3,542,867 and 3,542,875 in that it contains less by-product acrylamide as an impurity.

In general, the prior art teaches the preparation of DIAC by reacting acrylonitrile and 4-hydroxy-4-methyl-2pentanone in the presence of at least 93% sulfuric acid, the mole ratios of said sulfuric acid and acrylonitrile to said 4-hydroxy-4-methyl-2-pentanone being about 1–2 and 1–1.5 moles, respectively, at a temperature below 15° C., allowing the reaction mixture to warm up to ambient to moderately elevated temperatures to complete the reaction, cooling the reaction mixture, contacting the reaction mixture with water and a water-immiscible organic solvent, neutralizing the aqueous phase with an alkalizing agent, separating the organic phase, stripping the organic phase of volatile materials, and recovering N-(1,1-dimethyl-3-oxobutyl)acrylamide therefrom.

DIAC is useful in photographic films, adhesives, as a reactive cross-linking monomer in unsaturated polyester resins, as a stabilizer in paper and glass reinforced prepregs, and as an additive in hydrocarbon oils. For a description of how to use as an oil additive, see for example, U.S. Pat. No. 3,227,056, Example 18, which is incorporated herein by reference.

In order to obtain DIAC of acceptable color and purity for use in photographic films, it has been generally necessary either to distill or recrystallize the crude product.

There is a need, therefore, for a process that will give high yields of essentially colorless DIAC, having a melting point above 54° C., which does not have to be purified by subsequent recrystallization or distillation.

SUMMARY OF THE INVENTION

In accordance with the present invention, there is provided a process for preparing diacetone acrylamide which comprises (1) contacting a dispersion of 5,6-dihydro-6-hydroxy-4,4,-6-trimethyl-2-vinyl-1,3,4H)-oxazine sulfate (1:1) in a water-immiscible organic solvent with a neutralizing or alkalizing amount of gaseous ammonia at a temperature between about 10° C., and 30° C. to form a solution of diacetone acrylamide in said organic solvent and a precipitate of crystalline ammonium sulfate; (2) separating the crystals of ammonium sulfate; (3) cooling the organic mother liquors recovered from step (2) to about −10° C. to 20° C. to crystallize N-(1,1-dimethyl-3-oxobutyl)acrylamide therefrom; and (4) recovering the crystals of N-(1,1-dimethyl-3-oxobutyl)acrylamide, washing with a cold water-immiscible organic solvent, and drying the same.

In a preferred embodiment, the additional steps of (a) contacting the organic phase recovered from step (2) with a decolorizing agent, optionally also with a filter aid, and (b) separating said decolorizing agent, and optional filter aid, from the organic phase are carried out before carrying out steps (3) and (4).

In an especially preferred embodiment, the mother liquor plus wash liquor recovered in step (4) is diluted with 10-20% by volume of fresh organic solvent and recycled in step (1).

In addition to the advantages previously described, the present invention eliminates the need for azeotropically drying and concentrating the organic solution containing the desired product, and offers better environmental control.

DESCRIPTION OF PREFERRED EMBODIMENTS

The various stages of the process are described below in detail:

(1 Ammonolysis of the Compound of Formula (I)

The compound of formula (I) is added to a stirred water-immiscible organic solvent in which DIAC is soluble using about 1.75-2.75 mls, preferably about 1.7-1.8 mls, of said water-immiscible organic solvent per gram of the compound of formula (I) to form a dispersion. Suitable water-immiscible organic solvents include naphtha, chloroform, methyl isobutyl ketone, dibutyl ether, aromatic hydrocarbons such as benzene, toluene, xylene, and the like. The preferred water-immiscible organic solvent is toluene.

The dispersion is cooled to about 10°-30° C., preferably to about 15°-20° C., and gaseous ammonia is bubbled in to the reaction mixture to neutralize or alkalize the compound of formula (I) and form a two-phase mixture of a solution of DIAC in the water-immiscible organic solvent and a precipitate of by-product ammonium sulfate. Preferably, the amount of ammonia added is about 1.5-5.5% molar excess over that required to neutralize the compound of formula (I).

In terms of grams of ammonia per gram of compound of formula (I) added, the amount ranges from about 0.128 to 0.15, preferably about 0.13 to 0.135.

(2) The Separation of Ammonium Sulfate

Separation of the ammonium sulfate is carried out by conventional methods such as filtration or centrifuging to provide an organic mother liquor containing DIAC dissolved therein.

(3) The Crystallization of DIAC

The organic mother liquor recovered from (2) is cooled to about −10° C. to 20° C., preferably about −8° C. to 10° C., and held thereat for about ½-4 hours, preferably about 1-2 hours, to crystallize the DIAC from the solution.

Preferably, the organic mother liquor recovered from (2) is stirred with about 0.01 to 0.1, preferably about 0.03 to 0.04, part by weight of a decolorizing agent per part by weight of the compound of formula (I) used, at about 30°-45° C., preferably about 30°-35° C., for about ½-1 hour to remove colored impurities; the mixture is then clarified before cooling to crystaillize DIAC therefrom.

Suitable decolorizing agents include materials such as Super-Filtrol® (Filtrol Corp.), an acidified clay; Alcoa F-1 (Aluminum Corp. of America), an activated alumina; Darco® G-60 Decolorizing Carbon (Atlas Chemical Industries, Inc.); RB Carbon, and the like. The preferred decolorizing agent is Super-Filtrol®, used in an amount of about one part by weight per 50 parts by volume of solution treated.

Preferably, about 0.012 part by weight of a filter aid, such as Hyflo Super-Cel® (Johns-Manville), per part by weight of the compound of formula (I) is added to the organic solution prior to clarification to facilitate the removal of the decolorizing agent.

After clarification, the residual decolorizing agent and filter aid are washed with about 0.05 to 0.1 ml of water-immiscible organic solvent per gram of compound of formula (I) used, preferably toluene, and the washings are added to the clarified solution. The clarified solution plus wash liquor is then cooled, as described previously, to crystallize the DIAC therefrom.

(4) The Recovery of Crystalline DIAC

The crystalline DIAC is recovered by conventional means, washed with cold water-immiscible solvent, preferably toluene at −8° C., or lower, and dried. The initial yield of DIAC based on the compound of formula (I) is about 63-71% of theoretical.

In an especially preferred embodiment, the mother liquor plus wash liquor recovered in (4) is diluted with 10-20%, preferably about 15%, by volume of fresh water-immiscible organic solvent, preferably toluene, and recycled in (1). Recycling the mother liquor from (4) to (1) increases the yield of DIAC to about 70-80% of theoretical.

The final product obtained melts above 54° C., and contains less than 0.1% by weight of acrylamide.

The following examples further illustrate the invention. All parts and percentages are by weight unless otherwise specified. All ranges expressed are inclusive of both numbers.

EXAMPLE 1

Preparation of
5,6-Dihydro-6-Hydroxy-4,4,6-Trimethyl-2-Vinyl-1,3(4H)-Oxazine Sulfate (1:1)

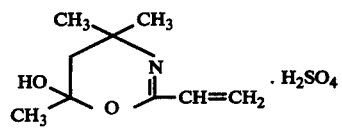

Sulfuric acid (392 grams; 98% real; 3.92 moles) is cooled to 0° C., and a mixture of acrylonitrile (113.5 grams; 2.14 moles) and diacetone alcohol (203.5 grams; 1.75 moles) is added thereto over 1.5 hours while maintaining the temperature at 0-5° C. The resulting mixture is stirred at 0-5° C. for 0.5 hour, allowed to warm up slowly to 40-42° C., held thereat for 3 hours and then cooled at 15° C. Acetone (443 grams; 0.625 ml./gram of reaction mixture) is added to the reaction mixture while keeping the temperature at 15-20° C. Upon completion of the addition, the solution is cooled to 0-5° C., and held thereat for 4 hours. The resulting crystals are separated by filtration, washed with acetone and dried to obtain 234 grams of product. The yield of product is 50% of theoretical based on diacetone alcohol.

Calculated for $C_9H_{17}NO_6S$: C,40.45%; H,6.41%; N,5.24%; S,11.97%. Found: C,39.77%; H,6.35%; N,5.10%; S,11.74%; $H_2O$, 1.55%.

Corrected for 1.55% $H_2O$: C,40.40%; H,6.28%; N,5.18%; S,11.93%.

Calculated for % $H_2SO_4$: 36.7%. Found: 36.6%.

EXAMPLE 2

The product of Example 1 (170 grams; 0.637 mole) is stirred with toluene (450 mls) to form a slurry and gaseous ammonia is bubbled into the slurry, while allowing the temperature to rise to 30° C., until the ammonia is no longer taken up by the reaction mixture. The reaction mixture is then cooled to 15° C., and a white crystalline material is separated by filtration and rinsed with toluene. The combined filtrate and wash liquor is then concentrated under vacuum to a volume of 170 mls, and cooled at 5° C. overnight. The resulting slurry is filtered to collect the crystalline precipitate and the crystals are washed with 100 mls of toluene (−10° C.). The solid is then dried to obtain 68.18 grams of DIAC, 63.28% of theoretical, m.p. 55.4–57.2° C.

EXAMPLE 3

The product of Example 1 (170 grams; 0.637 mole) is stirred with toluene (250 mls) to form a slurry and treated with gaseous ammonia as described in Example 2. The reaction mixture is then cooled to 15°–20° C., stirred thereat for 2 hours, and filtered to separate the white crystals. The crystals are washed with toluene (50 mls) and the combined filtrate and wash liquor Cel ® (2 grams) at 30° C. for 30 minutes. The insolubles are then separated by filtration and washed with toluene (10 mls). The combined filtrate plus wash liquor is cooled to 5°–10° C., and aged thereat for one hour to crystallize the product. The resulting crystals are recovered by filtration, washed with cold (−10° C.) toluene (50 mls) and dried. The yield of DIAC is 59.2 grams, 55% of theoretical, m.p. 55.2°–57.0° C.

In the manner described above, omitting the Super-Filtrol ® and Hyflo Super-Cel ®, the product obtained is slightly colored.

We claim:

1. A process for preparing N-(1,1-dimethyl-3-oxobutyl)acrylamide which comprises (1) contacting a dispersion of 5,6-dihydro-6-hydroxy-4,4,6-trimethyl-2-vinyl-1,3(4H)-oxazine sulfate (1:1) in a water-immiscible organic solvent with a neutralizing or alkalizing amount of gaseous ammonia at a temperature between about 10° C. and 30° C. to form a solution of diacetone acrylamide in said organic solvent and a precipitate of crystalline ammonium sulfate; (2) separating the crystals of ammonium sulfate; (3) cooling the organic mother liquors recovered from step (2) to about −10° C. to 20° C. to crystallize N-(1,1-dimethyl-3-oxobutyl)acrylamide therefrom; and (4) recovering the crystals of N-(1,1-dimethyl-3-oxobutyl)acrylamide, washing the recovered crystals with a cold water-immiscible organic solvent, and drying the same.

2. The process of claim 1 which includes the additional steps of (a) contacting the organic mother liquor recovered from step (2) with a decolorizing agent, and (b) separating said decolorizing agent from said organic mother liquor before carrying out steps (3) and (4).

3. The process of claim 2 wherein said decolorizing agent is an acidified clay.

4. The process of claim 1 wherein said water-immiscible organic solvent is toluene.

5. The process of claim 1 wherein mother liquor and wash liquor recovered in step (4) are combined, diluted with 15–20% by volume of fresh water-immiscible solvent, and recycled in step (1).

6. The process of claim 2 wherein mother liquor and wash liquor recovered in step (4) are combined, diluted with 15–20% by volume of fresh water-immiscible solvent, and recycled in step (1).

* * * * *